(12) United States Patent
Rubin et al.

(10) Patent No.: US 7,156,895 B2
(45) Date of Patent: Jan. 2, 2007

(54) AIR CLEANING SYSTEM

(76) Inventors: David Rubin, 8949 Montrose Way, San Diego, CA (US) 92122; Eyal Rubin, 8949 Montrose Way, San Diego, CA (US) 92122

( * ) Notice: Subject to any disclaimer, the term of this patent is extended or adjusted under 35 U.S.C. 154(b) by 0 days.

(21) Appl. No.: 10/751,938

(22) Filed: Jan. 7, 2004

(65) Prior Publication Data

US 2005/0145108 A1    Jul. 7, 2005

(51) Int. Cl.
   *B01D 47/02*    (2006.01)
(52) U.S. Cl. ............... 95/8; 95/223; 95/226; 96/244; 96/351
(58) Field of Classification Search ............... 95/8, 95/223, 226, 228; 96/244, 279, 351–354, 96/342–345; 261/121.1–126
   See application file for complete search history.

(56) References Cited

U.S. PATENT DOCUMENTS

| | | | | |
|---|---|---|---|---|
| 3,486,307 A | * | 12/1969 | McDermott | ............... 96/257 |
| 4,850,117 A | * | 7/1989 | Venkat et al. | ............... 34/470 |
| 5,009,869 A | | 4/1991 | Weinberg et al. | |
| 5,078,759 A | * | 1/1992 | Kira | ............... 95/223 |
| H001189 H | | 5/1993 | Kirts | |
| 5,227,144 A | | 7/1993 | Perez De La Garza | |
| 5,449,398 A | * | 9/1995 | Motoda | ............... 95/175 |
| 5,453,107 A | * | 9/1995 | Liu | ............... 96/344 |
| 5,512,262 A | | 4/1996 | Shimada et al. | |
| 5,662,872 A | | 9/1997 | Shimada et al. | |
| 5,670,122 A | | 9/1997 | Zamansky et al. | |
| 5,743,944 A | * | 4/1998 | Gross et al. | ............... 96/181 |
| 5,858,072 A | * | 1/1999 | Motoda | ............... 96/332 |
| 6,068,686 A | * | 5/2000 | Sorensen et al. | ............... 96/135 |
| 6,379,638 B1 | | 4/2002 | Matacotta et al. | |
| 6,511,640 B1 | | 1/2003 | Kumar et al. | |
| 2002/0064486 A1 | | 5/2002 | Shimakawa | |
| 2003/0082918 A1 | | 5/2003 | Hayasaka et al. | |

FOREIGN PATENT DOCUMENTS

| | | |
|---|---|---|
| EP | 0 624 392 | 5/1994 |
| EP | 0 625 368 | 5/1994 |
| JP | 6319946 | 11/1994 |

* cited by examiner

*Primary Examiner*—Frank M. Lawrence
(74) *Attorney, Agent, or Firm*—Browdy and Neimark, PLLC

(57) ABSTRACT

A system for cleaning air wherein the air to be cleaned is bubbled up through an aqueous phase and an organic phase. The air is bubbled upwardly through the liquid to take advantage of the weight of the liquid to compress the gas, thereby increasing the solubility of the gas in the liquid. Because of specific gravity, the aqueous phase is generally at the bottom of at least one cylinder or container, and the organic phase is generally on top of the aqueous phase. Gases are removed either continuously or periodically to ensure that there are adequate reagents in the aqueous and organic phases, so that the reagents therein can be replaced as needed. There is no limit to the number of cylinders that can be used, depending upon the impurity and thus the amount of reagents to be used in treating the air.

12 Claims, 1 Drawing Sheet

AIR CLEANING SYSTEM

FIELD OF THE INVENTION

The present invention relates to a method and apparatus for removing undesirable gases and microorganisms from air.

BACKGROUND OF THE INVENTION

There is an increasing amount of pollution in the air we breathe in the work environment, homes, hospitals, public buildings, and vehicles, caused by a variety of toxic, volatile, and often malodorous and irritating chemicals. Also included in this pollution are potentially dangerous microorganisms such as viruses, bacteria, molds, yeasts, spores, and other pathogens.

In industry, toxic, hazardous, or contaminating chemical vapors, such as formaldehyde, benzene, chloroform, etc., have come under strict government regulation. However, there is often an accumulation of these airborne pollutants in the vicinity of chemical plants, food processing operations, sewage treatment plants, and utilities. Significant or even larger contaminant or pollutant levels can occur indoors because of tightly enclosed more energy efficient buildings.

Additionally, there is now the threat of terrorism in which dangerous chemicals or microorganisms are introduced into the atmosphere.

Six criteria pollutants were originally named by the Environmental Protection Agency, which is required to summarize published information on each of these pollutants, the documents referred to as criteria documents. These pollutants are sulfur dioxide, carbon monoxide, nitrogen dioxide, ozone, suspended particulates and volatile organic compounds. These pollutants are ubiquitous, and there is substantial evidence linking them to health effects at high concentrations. Three of them, ozone, sulfur dioxide and nitrogen dioxide, are also considered phytotoxins, and these substances are fairly easy to measure.

A variety of methods are currently used for removing pollutants from air, including adsorption e.g., in activated carbons, absorption in solution, filtration, coagulation, electrostatic precipitation, incineration, chemical reaction, condensation, etc. However, many of these methods cannot readily remove very tiny particles, such as gas molecules.

Absorption of toxic gases by water or aqueous solutions, such as HCl, $NH_3$, HF, $Cl_2$, $H_2S$, amines, and the like, can be very effective. Likewise, many of these gases can be removed effectively by adsorption onto solid surfaces, particularly activated carbons. Absorption, adsorption, filtration, coagulation and electrostatic precipitation are physical methods of decontamination. Physical methods are of special interest where recovery of chemicals is economically desirable.

Chemical methods of decontamination include reactions of toxic or hazardous substances with oxidizing agents such as chlorine, chlorine dioxide, hypochlorite, ozone, peroxide, or reducing agents, such as dithionite, noble metal catalysts with hydrogen, metallic sodium, etc.

Both physical and chemical methods have drawbacks. For example, in a situation in which it is not desirable to recover airborne chemicals for reuse, the problems of disposal still exist. Additionally, physical techniques may suffer from saturation of the agent used to remove the pollutant. Chemical methods often require the use of reagents which are themselves quite toxic and often have problems of byproduct disposal. Other methods, such as incineration, can be uneconomical or even illegal in certain areas.

Perez de la Garza, in U.S. Pat. No. 5,227,144, discloses a process for decontaminating air to eliminate toxic gases. Air is circulated in a soaking chamber through air-permeable barriers that are continuously bathed in solutions containing chemical reagents which remove toxic, solid and gaseous pollutants from the air. The first barrier contains water to eliminate all solid particles suspended in the gas flow and to begin eliminating carbon monoxide. The second barrier contains an alkali metal hydroxide to eliminate nitrogen dioxide, hydrogen sulfide and prussic acid, as well as some of the ozone. The third barrier contains sulfuric acid to eliminate carbon monoxide. The fourth barrier contains an alkali earth hydroxide to eliminate carbon dioxide. The fifth barrier contains sodium nitrite to eliminate ozone. The sixth barrier contains potassium permanganate to eliminate sulfur dioxide. The seventh barrier contains a diluted solution of sodium hypochlorite to eliminate all vestiges of any of the reagents.

Kirts, in H1189, a Statutory Invention Registration, discloses a method for destroying chemical and biological warfare agents by heating contaminated air in a compressor by adiabatic compression, flowing the compressed hot air through a reaction vessel to provide sufficient contact time to kill chemical and biological warfare agents, partially cooling the hot compressed air in an aftercooler, and finally cooling the hot compressed air by expansion in a turbine.

Weinberg et al., in U.S. Pat. No. 5,009,869, disclose a method for treating air contaminated with chemical and biological pollutants in a closed system which includes an electrochemical reactor to regenerate the reagents. Contaminated air is treated in a wet scrubber zone containing a high surface area packing which is inert to the circulating aqueous scrubber liquid-electrolyte. The scrubber liquid-electrolyte may be circulated in a loop forming a closed system from the anode compartment of a cell to the wet scrubber zone wherein the polluted air is cleaned and the chemical and biological contaminates dissolved into liquid where they may be further broken down to products of substantially less hazard or toxicity. The scrubber liquid-electrolyte contains at least one electrochemically regeneratable degradant, such as a redox couple which in their active form chemically degrade, destroys, or disinfects the pollutant-containing scrubber-electrolyte. Ions are provided in the scrubber liquid-electrolyte to provide for ionic conductivity in the electrochemical cell. This system can be adapted to heating and cooling systems of buildings.

Zamansky et al., in U.S. Pat. No. 5,670,122, disclose a method for removing air pollutants from combustion gases by treating the gases with hydrogen peroxide or a mixture of hydrogen peroxide and methanol to remove one or more of nitric oxide, sulfur trioxide, light hydrocarbons, carbon monoxide, and trace amounts of mercury from combustion flue gas streams.

SUMMARY OF THE INVENTION

It is an object of the present invention to overcome the aforesaid deficiencies in the prior art.

It is another object of the present invention to provide a system for removing undesirable gases from air.

It is a further object of the present invention to destroy dangerous microorganisms in air, including viruses, bacteria, yeasts, molds, and spores.

According to the present invention, air, including its impurities and toxic, hazardous, or other undesirable gases and hazardous microorganisms, is flowed through at least one aqueous solution to remove the pollutants from the air, and subsequently through at least one organic solution to remove lipophilic and hydrophobic pollutants from air. Aqueous solutions are used to remove polar molecules that create electrovalent chemical bonds. An organic layer can be included to remove lipophilic or hydrophobic impurities that are lipid soluble and create covalent chemical bonds.

The aqueous phase contains compounds that have two properties:
1. The compounds do not react with each other; and
2. Each compound in the aqueous solution can react immediately with a toxic or undesirable gas and any microorganism that contaminates the air.

For purposes of the present invention, an "organic liquid" means a non-polar liquid, and these terms can be used interchangeably. The organic phase is used to trap or dissolve substances that are not removed in the aqueous phase.

The system of the present invention is based upon Raoul's law, namely, that the amount of gas dissolved in a liquid is directly proportional to the pressure of the gas on the liquid. Accordingly, the cylinders or tanks of liquids are placed vertically rather than horizontally. Air is bubbled into the liquid from the bottom of the container, going against the gravitational force exerted by the column of liquid, so that the air is under pressure in the container.

Liquids generally dissolve more gases when their temperatures are lower. For example, hydrogen peroxide or hydrogen chloride can be used to make a 30% solution in cold water (about 4° C.), but less than a 3% solution in boiling water. Accordingly, the cylinders are maintained at the lowest possible temperature which does not result in freezing of the water. The tanks can be refrigerated by the air conditioning system which is the post filter device of this system.

The examples given herein illustrate the use of cylindrical containers to hold the aqueous and organic phases. However, other types of containers known to those skilled in the art can be used to hold the liquids. The important criteria for the containers are that they contain means for creating micro bubbles in the gas as it enters the container, and that there is sufficient time for the gas to contact the aqueous and organic phases.

DETAILED DESCRIPTION OF THE INVENTION

Figure 1:
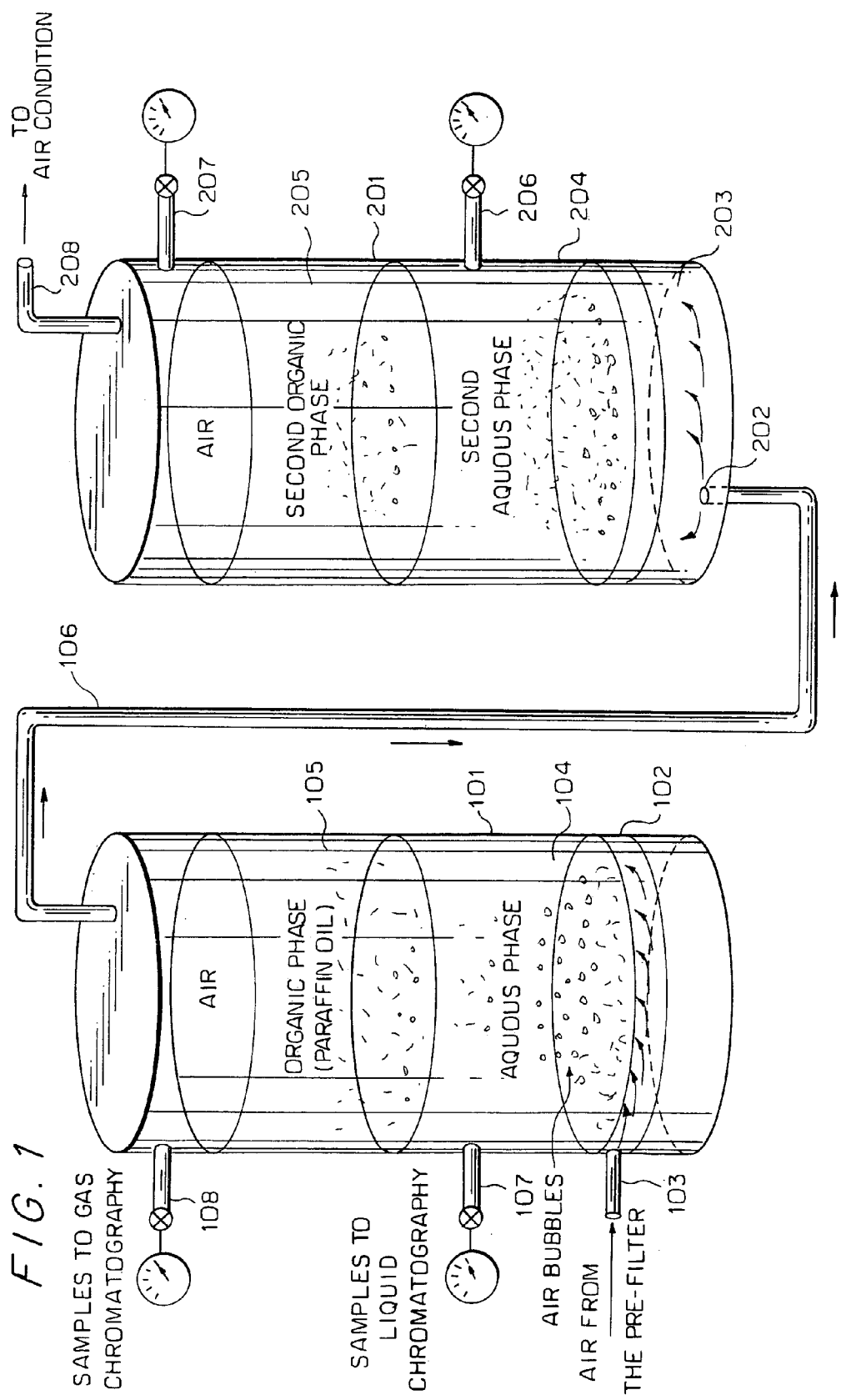
FIG. 1 shows a system for purifying air using two tanks or cylinders of liquid.

The present invention relies upon dissolving the impurities, toxic gases, and microorganisms in liquids, either aqueous or organic liquids. The aqueous solutions remove polar molecules and microorganisms, and the organic solutions remove lipophilic or hydrophobic impurities and toxic gases. Because gases are more soluble in cold liquids than hot liquids, the temperature of the liquids in the cylinders is preferably kept as low as possible without freezing the liquids, generally at about 4° C.

According to the present invention, gas to be cleaned is bubbled up through an aqueous phase and an organic phase. The gas is bubbled upwardly through the liquid to take advantage of the weight of the liquid to compress the gas, thereby increasing the solubility of the gas in the liquid. Because of specific gravity, the aqueous phase is generally at the bottom of the cylinder or container, and the organic phase is generally on top of the aqueous phase. Gases are removed either continuously or periodically to ensure that there are adequate reagents in the aqueous and organic phases, so that the reagents therein can be replaced as needed. While one cylinder or container can be used to treat gases, it may be desirable to have two or more cylinders, particularly when reagents are needed in the aqueous phase that would react with one another. In this situation, one noxious gas can be removed in a first cylinder, and another noxious gas removed in a subsequent cylinder, etc. There is no limit to the number of cylinders that can be used, depending upon the reagents to be used in treating the air.

Once the air has been conveyed through the requisite number of cylinders, the air is analyzed to ensure that all undesired components have been removed therefrom. If the air is determined to be acceptable, it is then conveyed to a conventional air conditioning, heating, or HVAC system. The microorganism initially present will be disintegrated in a way that their amino acid and nucleic acid components will dissolve in the liquid phase, while the lipids will dissolve in the organic phase.

The apparatus of the present invention 10 includes a conventional mechanical air filter that removes dust and small solid particles (not shown). This filter can be a HEPA filter, activated carbon, or any conventionally used filter material.

From the filter, air to be treated is introduced through an inlet 103 into a first vertical cylinder 101. At the bottom of the cylinder 101 is a disk 102 made of a plurality of perforated solid plates or sintered glass plates. The disk completely covers the bottom of the first cylinder, and air is introduced upwardly through the disc. This disc acts in much the same way as a bubbling stone in an aquarium to form micro bubbles in the liquid 104 above the disc.

Air is introduced into the first cylinder 101 through an inlet 103 from a conventional mechanical filter. The first cylinder 101 contains two liquid phases, namely, water 104 and a non-polar liquid such as paraffin oil 105 which floats on top of the water.

Each compound in the aqueous solution can react immediately with a toxic or undesirable gas as well as any microorganism that contaminates the air. The organic, or nonpolar, liquid eliminates nonpolar organic molecules that are not removed or destroyed by the aqueous solution.

In order to ensure that the aqueous solution contains sufficient reagents to purify the air, air is continuously sampled through a pipe 107 in the aqueous phase of the first cylinder 104 that connects to a liquid chromatograph (not shown). In the same manner, air is continuously sampled as it comes from the organic phase 105 through a pipe 108 to a gas chromatograph to ensure that the organic phase is sufficient for treating the air.

After being passed upwardly through the first cylinder, the air flows into a tube 106 through which the air is conveyed through an inlet 202 to a second cylinder 201. This second cylinder is equipped with a disc 203 made of perforated solid plates or sintered glass plates. This disc completely covers the bottom of the second cylinder 201, and the air is directed upwardly through the disc.

As in the first cylinder, the second cylinder 201 is equipped with pipes 206 and 207 that convey air from the aqueous or organic phase, respectively, to a liquid or gas chromatograph to ensure the efficacy of the treating reagents.

At the final outlet for the gas 208, the air is continuously sampled and assayed by a gas chromatograph to check for the purity of the air (i.e., the contaminants in the air have been eliminated). Once it has been determined that the samples are not contaminated, a micro switch is operated to bypass the rest of the cylinder 201 to convey the air through an outlet 208 to the intake for an air conditioning or heating system.

The apparatus of the present invention is part of a conventional air conditioning system which may be combined with a heating system which is constructed in such a way that the air conditioning system also cools the cylinders 101 and 201.

While the system has been illustrated with two vertical cylinders, the system may contain one or more than two vertical cylinders, depending upon the volume of air to be treated and the degree of contamination of the air. The air is pushed through the system by an air pump. Its dimensions and horse power are dependent upon the size/volume of space to be ventilated.

For the present invention, an undesirable or toxic gas includes gasses which are hazardous to organisms, including humans, or harmful to the environment, as well as hazardous gases of inflammable or explosive nature, gases with unpleasant odors, and gases containing the hazardous or unpleasant gases. Examples of noxious gases include ethylene oxide, toluene, acetone, as well as inorganic gases such as ammonia.

The aqueous phase contains reagents which react with noxious gases and render these gases harmless or inoffensive, as well as sterilants which destroy microorganisms. Examples of reagents to be included in the aqueous solution are:

1. 20–30%–20–40% by weight hydrogen peroxide, which destroys microorganisms such as anthrax, small pox virus, mold and, fungi 20–40%; converts carbon monoxide to carbon dioxide, and oxidizes hydrogen sulfide to sulfur dioxide.
2. potassium hydroxide, which converts carbon dioxide to the salt potassium carbonate, which remains in solution; sulfur dioxide in water reacts with water to produce sulfurous acid, which reacts with the potassium hydroxide to form the salt $K_2SO_3$.
3. Potassium permanganate, which reacts and destroys the nerve gas sarin and other acetylcholinesterase inhibitors, as well as oxidizing sulfur dioxide to form sulfates such as potassium sulfate and manganese sulfate;
4. Sulfuric acid, which oxidizes carbon monoxide;
5. Sodium nitrite, which reacts with ozone to produce sodium nitrate and oxygen;
6. Sodium hypochlorite or chlorine dioxide, which destroy microorganisms.

The organic phase eliminates contaminants such as alkenes, alkanes, and aromatic lipophilic gases such as methane, propane, and the like. These gases remain in the organic phase because of the high affinity and high solubility of these gases in the organic solvent. Exhaust gases from vehicles containing hydrocarbons and PCB's also will remain captured in the organic phase.

Additionally, free fatty acids such as $C_7H_{15}COOH$ and catalysts such as magnesium monoperphythate can be dissolved in the organic phase to neutralize and destroy compounds such as sulfur mustard gas.

One skilled in the art can readily, without undue experimentation, determine which compounds are most effective in removing the desired pollutants and microorganisms from air.

The foregoing description of the specific embodiments of the present invention will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments.

It is to be understood that the phraseology or terminology employed herein is for the purpose of description and not of limitation. The means and materials for carrying out disclosed functions may take a variety of alternative forms without departing from the invention. Thus, the expressions "means to . . . " and "means for." as may be found the specification above, and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above, and it is intended that such expressions be given their broadest interpretation.

What is claimed is:

1. A method for removing undesired gases and microorganisms from air comprising introducing air into the bottom of at least one container while producing micro bubbles of the air in a liquid;
   wherein the at least one container holds an aqueous phase and an organic phase wherein air is at the top of the at least one container;
   the aqueous phase contains compounds to remove or destroy undesired gases and microorganisms from the air which are hydrophilic in character, and the organic phase contains compounds to remove or destroy undesired gases and microorganisms which are lipophilic in character.

2. The method according to claim 1, wherein the containers are maintained at a temperature slightly above the freezing point of the liquids in the container.

3. The method according to claim 1 wherein the air is passed through at least two containers.

4. The method according to claim 1 wherein the aqueous phase contains a compound selected from the group consisting of hydrogen peroxide, potassium permanganate, sulfuric acid, sodium nitrite, sodium hypochiorite, and chlorine dioxide.

5. The method according to claim 1 wherein the organic phase contains a compound selected from the group consisting of free fatty acids and magnesium mono-perhydrate.

6. The method according to claim 1 wherein the air at the top of each container is assayed for purity and, if the air is pure, a switch is operated to convey the air out of the container.

7. An apparatus for cleaning air comprising:
   a. at least one container, each of said at least one container including an aqueous phase and an organic phase;
   b. an inlet at the bottom of the container for introducing air to be cleaned;
   c. means at the bottom of the container adapted and constructed to produce micro bubbles when air is introduced into the bottom of the container;
   d. an outlet at the top of the container to discharge clean air.

8. The apparatus according to claim 7 wherein at least two containers are provided, and wherein the at least two containers are connected by a tube leading from an outlet from the top of a first container to an inlet at the bottom of a subsequent container.

9. The apparatus according to claim 7 wherein the apparatus comprises at least two containers and a pipe connecting the at least two containers leads to a sampling device for sampling air for analysis.

10. The apparatus according to claim 7 further comprising a micro switch near the outlet of the container to release air that has been determined to be adequately cleaned.

11. The apparatus according to claim 7 wherein the means to produce microbubbles when air is introduced into the bottom of the container is a disc made of material selected from the group consisting of perforated solid plates and sintered glass plates.

12. The apparatus according to claim 7, further including means for refrigerating the containers.

* * * * *